(12) United States Patent
Holliday

(10) Patent No.: US 8,187,259 B2
(45) Date of Patent: May 29, 2012

(54) SYSTEM AND METHOD FOR STABILIZING DELIVERED LASER ENERGY

(75) Inventor: Keith Holliday, San Jose, CA (US)

(73) Assignee: AMO Manufacturing USA, LLC., Santa Ana, CA (US)

( * ) Notice: Subject to any disclaimer, the term of this patent is extended or adjusted under 35 U.S.C. 154(b) by 10 days.

(21) Appl. No.: 12/903,507

(22) Filed: Oct. 13, 2010

(65) Prior Publication Data

US 2011/0028956 A1    Feb. 3, 2011

Related U.S. Application Data

(62) Division of application No. 11/077,173, filed on Mar. 9, 2005, now Pat. No. 7,836,893.

(60) Provisional application No. 60/553,580, filed on Mar. 15, 2004.

(51) Int. Cl.
*A61B 18/20* (2006.01)
(52) U.S. Cl. .................. 606/12; 606/5; 606/10; 606/11
(58) Field of Classification Search .................. 606/4–6, 606/10–12; 607/88–94; 128/898; 356/213–236; 219/121.6, 121.61, 121.62
See application file for complete search history.

(56) References Cited

U.S. PATENT DOCUMENTS

| | | | |
|---|---|---|---|
| 3,768,908 A | 10/1973 | Zaromb | |
| 4,023,408 A | 5/1977 | Ryan et al. | |
| 4,156,182 A | 5/1979 | Brick et al. | |
| 4,198,599 A | 4/1980 | Krider et al. | |
| 4,395,906 A | 8/1983 | Ryan et al. | |
| 4,422,037 A | 12/1983 | Coleman | |
| 4,461,294 A | 7/1984 | Baron | |
| 4,506,211 A | 3/1985 | Coleman | |
| 4,665,913 A | 5/1987 | L'Esperance, Jr. | |
| 4,669,466 A | 6/1987 | L'Esperance | |
| 4,718,418 A | 1/1988 | L'Esperance, Jr. | |
| 4,729,372 A | 3/1988 | L'Esperance, Jr. | |
| 4,732,148 A | 3/1988 | L'Esperance, Jr. | |
| 4,770,172 A | 9/1988 | L'Esperance, Jr. | |
| 4,773,414 A | 9/1988 | L'Esperance, Jr. | |
| 4,798,204 A | 1/1989 | L'Esperance, Jr. | |

(Continued)

FOREIGN PATENT DOCUMENTS

WO      WO 91/08723 A1    6/1991

(Continued)

OTHER PUBLICATIONS

Munnerlyn et al., "Photoreactive keratectomy: A technique for laser refractive surgery" J. Cataract Refract. Surg. (1988) 14:46-52.

(Continued)

*Primary Examiner* — Ahmed Farah
(74) *Attorney, Agent, or Firm* — AMO Manufacturing USA, LLC.

(57) ABSTRACT

Systems and methods provide for stabilizing the amount of laser energy delivered to a target from a laser device. Generally, delivered laser energy is measured over multiple laser pulses or over time in the case of a constant wave laser. A decrease is then calculated in the delivered energy, the decrease being caused by accumulation of one or more substances, such as ozone, along the laser beam delivery path due to passage of the laser beam along the path. Using this calculated decrease, a laser device may be adjusted to compensate for the decrease in delivered energy due to the accumulated substance(s), thus stabilizing the amount of energy delivered to the target.

6 Claims, 6 Drawing Sheets

U.S. PATENT DOCUMENTS

| | | | |
|---|---|---|---|
| 4,806,851 | A | 2/1989 | Krider et al. |
| 4,840,175 | A | 6/1989 | Peyman |
| 4,862,888 | A | 9/1989 | Yessik |
| 4,873,483 | A | 10/1989 | Ostrander |
| 4,901,718 | A | 2/1990 | Bille et al. |
| 4,903,695 | A | 2/1990 | Warner et al. |
| 4,907,586 | A | 3/1990 | Bille et al. |
| 4,911,711 | A | 3/1990 | Telfair et al. |
| 4,947,047 | A | 8/1990 | Muraki |
| 4,973,330 | A | 11/1990 | Azema et al. |
| 5,074,859 | A | 12/1991 | Koziol |
| 5,090,798 | A | 2/1992 | Kohayakawa |
| 5,144,630 | A | 9/1992 | Lin |
| 5,157,676 | A | 10/1992 | Wilcox |
| 5,163,934 | A | 11/1992 | Munnerlyn |
| 5,219,344 | A | 6/1993 | Yoder, Jr. |
| 5,282,014 | A | 1/1994 | Ruhl, Jr. et al. |
| 5,284,477 | A | 2/1994 | Hanna et al. |
| 5,295,072 | A | 3/1994 | Stevens, Jr. et al. |
| 5,305,210 | A | 4/1994 | Kuzma et al. |
| 5,309,186 | A | 5/1994 | Mizuno |
| 5,331,330 | A | 7/1994 | Susnjara |
| 5,342,351 | A | 8/1994 | Blaha et al. |
| 5,355,253 | A | 10/1994 | Nanjo et al. |
| 5,395,356 | A | 3/1995 | King et al. |
| 5,445,633 | A | 8/1995 | Nakamura et al. |
| 5,470,329 | A | 11/1995 | Sumiya |
| 5,500,602 | A | 3/1996 | Youngquist |
| 5,500,697 | A | 3/1996 | Fujieda |
| 5,502,371 | A | 3/1996 | Youngquist |
| 5,507,799 | A | 4/1996 | Sumiya |
| 5,528,494 | A | 6/1996 | Moses |
| 5,544,182 | A | 8/1996 | Nagaishi et al. |
| 5,610,813 | A | 3/1997 | Greenewald et al. |
| 5,624,436 | A | 4/1997 | Nakamura et al. |
| 5,637,109 | A | 6/1997 | Sumiya |
| 5,643,249 | A | 7/1997 | Amano |
| 5,646,791 | A | 7/1997 | Glockler |
| 5,683,379 | A | 11/1997 | Hohla |
| 5,699,245 | A | 12/1997 | Herold |
| 5,713,892 | A | 2/1998 | Shimmick |
| 5,742,626 | A | 4/1998 | Mead et al. |
| 5,767,519 | A * | 6/1998 | Gelbwachs .................. 250/372 |
| 5,912,775 | A | 6/1999 | Glockler |
| 5,980,101 | A | 11/1999 | Unternahrer et al. |
| 6,002,706 | A * | 12/1999 | Staver et al. .................. 372/108 |
| 6,203,539 | B1 | 3/2001 | Shimmick et al. |
| 6,210,401 | B1 * | 4/2001 | Lai .................................. 606/12 |
| 6,245,059 | B1 | 6/2001 | Clapham |
| 6,280,435 | B1 | 8/2001 | Odrich et al. |
| 6,319,247 | B1 | 11/2001 | Hofer et al. |
| 6,322,555 | B1 | 11/2001 | LaHaye |
| 6,331,177 | B1 | 12/2001 | Munnerlyn et al. |
| 6,347,549 | B1 | 2/2002 | Ryan et al. |
| 6,396,577 | B1 | 5/2002 | Ramstack |
| 6,419,671 | B1 | 7/2002 | Lemberg |
| 6,436,093 | B1 | 8/2002 | Ruiz et al. |
| 6,673,062 | B2 | 1/2004 | Yee et al. |
| 6,726,680 | B1 | 4/2004 | Knopp et al. |
| 6,793,654 | B2 | 9/2004 | Lemberg |
| 7,836,893 | B2 | 11/2010 | Holliday |

FOREIGN PATENT DOCUMENTS

| | | |
|---|---|---|
| WO | WO 91/11158 A1 | 8/1991 |
| WO | WO 92/13507 A1 | 8/1992 |
| WO | WO 93/08877 A1 | 5/1993 |
| WO | WO 93/14430 A1 | 7/1993 |
| WO | WO 95/27535 A1 | 10/1995 |
| WO | WO 01/10322 A1 | 2/2001 |
| WO | WO 03/090867 A1 | 11/2003 |

OTHER PUBLICATIONS

Sher et al., "Clinical Use of the 193-nm Excimer Laser in the Treatment of Corneal Scars," Arch Ophthalmol. Apr. 1991;109(4):491-8.

Stark et al., "Clinical Follow-up of 193-nm ArF Excimer Laser Photokeratectomy", Ophthalmology. May 1992;99(5):805-12.

\* cited by examiner

SYSTEM AND METHOD FOR STABILIZING DELIVERED LASER ENERGY

CROSS REFERENCE TO RELATED APPLICATIONS

The present application is a Divisional of U.S. Ser. No. 11/077,173 filed Mar. 9, 2005 (Allowed), which application claims priority from U.S. Provisional Application No. 60/553,580 filed Mar. 15, 2004; the full disclosures of which are hereby incorporated by reference in their entirety for all purposes.

BACKGROUND OF THE INVENTION

The present invention relates generally to laser eye surgery methods and systems. More specifically, the present invention relates to methods and systems for stabilizing an amount of laser energy delivered to a target.

Known laser eye procedures generally employ an ultraviolet or infrared laser to remove a microscopic layer of stromal tissue from the cornea of the eye to alter the refractive characteristics of the eye. The laser removes a selected shape of the corneal tissue, often to correct refractive errors of the eye. Ultraviolet laser ablation results in photo-decomposition of the corneal tissue, but generally does not cause significant thermal damage to adjacent and underlying tissues of the eye. The irradiated molecules are broken into smaller volatile fragments photochemically, directly breaking the intermolecular bonds.

Laser ablation procedures can remove the targeted stroma of the cornea to change the cornea's contour for varying purposes, such as for correcting myopia, hyperopia, astigmatism, and the like. Control over the distribution of ablation energy across the cornea may be provided by a variety of systems and methods, including the use of ablatable masks, fixed and moveable apertures, controlled scanning systems, eye movement tracking mechanisms, and the like. In known systems, the laser beam often comprises a series of discrete pulses of laser light energy, with the total shape and amount of tissue removed being determined by the shape, size, location, and/or number of a pattern of laser energy pulses impinging on the cornea. A variety of algorithms may be used to calculate the pattern of laser pulses used to reshape the cornea so as to correct a refractive error of the eye. Known systems make use of a variety of forms of lasers and/or laser energy to effect the correction, including infrared lasers, ultraviolet lasers, femtosecond lasers, frequency multiplied solid-state lasers, and the like. Known corneal correction treatment methods have generally been successful in correcting standard vision errors, such as myopia, hyperopia, astigmatism, and the like. By customizing an ablation pattern based on wavefront measurements, it may be possible to correct minor aberrations to reliably and repeatedly provide visual acuity greater than 20/20.

When laser energy is delivered from a laser energy generating device to a target, as in a laser eye surgery procedure, the energy (typically in the form of a laser beam) passes along a delivery path. The laser beam typically follows a path that proceeds through a series of lenses, mirrors and/or other optical elements to focus and/or direct the beam before it arrives at a patient's eye. As laser energy passes along such a delivery path, it typically causes one or more substances to accumulate. The most prevalent and significant substance that accumulates along a UV laser beam delivery path due to passage of the laser beam is ozone. The laser beam creates ozone when it passes through oxygen along the delivery path. Subsequent pulses of the laser beam are then impeded by the presence of ozone along the path, resulting in a reduced amount of energy arriving at the patient's eye with each subsequent pulse. The same reduction occurs over time with a constant wave laser. As ozone continues to accumulate, the laser energy arriving at the eye continues to decrease.

One objective in laser eye surgery is to deliver approximately the same amount of laser energy to the eye with each pulse of the laser, or if constant wave laser energy is used, to deliver a constant amount of energy to the eye over time. Currently available systems and techniques, however, do not account for accumulation of substances such as ozone along the laser beam delivery path, and thus do not provide a constant or stabilized amount of delivered laser energy to the eye. Stabilized delivered laser energy would enhance laser eye surgery by providing a desired amount of energy to an eye over multiple laser pulses and over time to allow for a more precise and accurate laser eye surgery procedure.

Therefore, it would be desirable to provide methods and systems for stabilizing an amount of laser energy delivered to an eye during a laser eye surgery procedure. Ideally, such methods and systems compensate for impedance of a laser beam caused by accumulation of substances, such as ozone, along the laser beam delivery path. Also ideally, such methods and systems could be used to calibrate a laser generating device before performing any laser eye surgery procedures and would not require frequent recalibrations. At least some of these objectives will be met by the present invention.

BRIEF SUMMARY OF THE INVENTION

The present invention generally provides methods and systems for enhancing delivery of laser energy to a target by helping to stabilize the amount of delivered energy. Delivered energy is stabilized by compensating for one or more accumulated substances, typically ozone, that form when a laser beam travels along its path from a laser generating device to a target. Once a reduction in delivered energy due to accumulated ozone and/or other substances is measured, an adjustment to a laser generating device may be calculated to compensate for the reduction in delivered energy. Although methods and systems of the invention are typically described for use in laser eye surgery, various embodiments may be used for stabilizing delivered laser energy for any other purpose, with any other laser device or the like. Thus, the present invention is not limited to use in laser eye surgery procedures or any other specific field.

In the following description, the terms "delivered energy" or "delivered laser energy" are often used. By delivered energy it is meant the energy that is delivered to a target, such as a patient's eye. In other words, delivered energy is the energy that actually arrives at the target. An amount of delivered energy may or may not be different than an amount of "provided laser energy," "dispatched laser energy," "sent laser energy," "energy directed from a laser device" or the like. By provided laser energy it is meant the energy that leaves a laser device or laser energy generating device. As is described above, an amount of energy that is provided by a laser energy generating device is often decreased as it travels along a laser beam delivery path, thus resulting in a decreased amount of delivered energy that arrives at the target. Such is the case, for example, when multiple laser beam pulses are directed along the delivery path. Earlier pulses cause oxygen to be converted to ozone, and the ozone impedes subsequent laser pulses from traveling along the path, thus reducing the amount of laser energy arriving at the target in subsequent pulses. In other words, if the subsequent pulses have the same amount of energy as they leave the laser energy generating device, they do not have the same amount of energy when they arrive at the target, due to interference from ozone and/or other substances accumulated along the delivery path. At any rate, none of the terminology defined above or used in the following descriptions should be interpreted to limit the scope of the invention. Any suitable terms may be used to describe an amount of laser energy leaving a device and an amount of energy arriving at (or "delivered to") a target.

That being said, in one aspect of the invention, a method for stabilizing an amount of laser energy delivered to a target by a laser generating device involves: measuring the amount of delivered laser energy arriving at or near a target from the laser generating device over a period of time; calculating a decrease in the amount of delivered energy over time; and adjusting the laser generating device to compensate for the decrease to stabilize the amount of delivered laser energy arriving at the target. In some embodiments, measuring the amount of delivered laser energy comprises measuring with a laser energy meter positioned at or near the target. For example, the laser energy meter may be positioned on an opposite side of a partially transparent lens or mirror from the target. In some embodiments, the laser energy comprises multiple pulses of laser energy, while in other embodiments the energy is constant wave (CW) laser energy.

As discussed above, in some embodiments calculating the decrease in the amount of delivered energy involves calculating a decrease caused by passage of the laser energy along a delivery path, which causes an accumulation of at least one substance along the delivery path, the substance impeding subsequent passage of the laser energy. For example, the substance that accumulates may comprise ozone, since passage of the laser energy along the delivery path typically causes an amount of oxygen ($O_2$) to be converted to ozone ($O_3$). Alternatively or additionally, the method may calculate a decrease in delivered energy based on accumulation of any other substance(s) along the laser energy delivery path. In some embodiments, calculating the decrease in the amount of delivered energy comprises calculating a decrease in delivered energy of a pulse of laser energy compared to an immediately previously fired pulse of laser energy. For example, calculating the decrease may involve calculating an amount of decrease caused by accumulation of one or more substances in the delivery path of the laser energy and reducing the amount of the decrease caused by the accumulation by a factor of time between pulses of the laser energy, which time allows for dissipation of the substance(s).

Adjusting the laser generating device, in some embodiments, comprises increasing an amount of laser energy provided from the laser generating device over time to compensate for accumulation of at least one substance along a delivery path of the laser energy caused by passage of the laser energy along the path. Again, the substance may be ozone and/or any other substance. In some embodiments, adjusting the laser generating device also involves reducing any increases in the amount of provided laser energy to compensate for time between pulses of laser energy, which time allows for dissipation of the substance(s).

Typically, though not necessarily, the measuring, calculating and adjusting steps of the method are performed during a calibration procedure for the laser generating device. A laser may thus be calibrated before performing a laser eye surgery procedure, and the laser may then be used for multiple procedures without recalibration. In some embodiments, the method also includes directing laser energy, either pulsed or constant wave, from the laser generating device toward the target. Some embodiments may also include performing a laser eye surgery procedure with the laser generating device after the calibration procedure.

In another aspect of the present invention, a method for performing a laser eye surgery procedure comprises calibrating a laser generating device and performing the laser eye surgery procedure using the calibrated laser generating device. Calibrating the laser generating device comprises: measuring the amount of delivered laser energy arriving at or near a target from the laser generating device over a period of time; calculating a decrease in the amount of delivered energy over time; and adjusting the laser generating device to compensate for the decrease so that the delivered laser energy arriving at the target remains approximately constant over time.

In another aspect of the invention, a method for performing a laser eye surgery procedure includes directing an amount of laser energy from a laser generating device toward an eye and adjusting the amount of directed laser energy to compensate for accumulation of one or more substances along a delivery path of the laser energy to stabilize the amount of delivered laser energy that arrives at the eye. As mentioned, typically the amount of directed laser energy is adjusted to compensate for accumulation of ozone along the delivery path, although it may alternatively or additionally be adjusted to compensate for accumulation of any other substance(s). In some embodiments, the amount of directed laser energy is increased over time to compensate for accumulation of ozone along the delivery path and is decreased over time to compensate for time between pulses of the laser energy, which time allows the ozone to dissipate.

In another aspect of the present invention, a system for performing a laser eye surgery procedure comprises: a laser energy generating device; a laser energy measuring device disposed at or near a target for measuring delivered energy of the laser energy device; and a processor coupled with the laser energy generating device and the laser energy measuring device. The processor is generally for calculating an adjustment to the laser energy generating device to compensate for accumulation of one or more substances along a laser energy delivery path and for adjusting the laser energy generating device to stabilize an amount of delivered laser energy that arrives at a target of the laser eye surgery procedure.

In various embodiments, the laser energy generating device may provide either pulsed laser energy, constant wave laser energy, or both. In some embodiments, as mentioned above, the processor is calibrated before performing the laser eye surgery procedure. Also in some embodiments, the processor increases an amount of laser energy provided by the laser energy device to compensate for the accumulation of the substance(s) and decreases the provided laser energy to compensate for time between pulses of the laser energy, which time allows for dissipation of the substance(s). Again, the system typically compensates for accumulation of ozone along the delivery path.

In yet another aspect of the present invention, a system for performing a laser eye surgery procedure includes a laser energy generating device and a processor coupled with the laser energy generating device for calculating an adjustment to the laser energy generating device to compensate for accumulation of one or more substances along a laser energy delivery path and for adjusting the laser energy generating device to stabilize an amount of delivered laser energy that arrives at a target of the laser eye surgery procedure. The processor is calibrated before performing the laser eye surgery procedure.

These and other aspects and embodiments of the invention are described in detail below, in reference to the attached drawing figures.

DETAILED DESCRIPTION OF THE INVENTION

The present invention is particularly useful for enhancing the accuracy and efficacy of laser eye surgical procedures, such as photorefractive keratectomy (PRK), phototherapeutic keratectomy (PTK), laser assisted in situ keratomileusis (LASIK), laser epithelial keratomileusis (LASEK) and the like. Preferably, the present invention can provide enhanced optical accuracy of refractive procedures by improving a corneal ablation of a refractive treatment program. While systems and methods of the present invention are described primarily in a context of a laser eye surgery system, techniques of the present invention may also be adapted for use in alternative eye treatment procedures and systems such as ablatable intraocular lenses, contact lenses, and the like. Additionally, systems and methods of the invention may be used in contexts outside of laser eye surgery for enhancing any laser device used for any purpose.

The techniques of the present invention can be readily adapted for use with existing laser systems. By helping stabilize an amount of laser energy delivered to a patient's eye, the present invention may facilitate sculpting of the cornea so that treated eyes regularly exceed a normal 20/20 threshold of desired vision.

Figure 1:
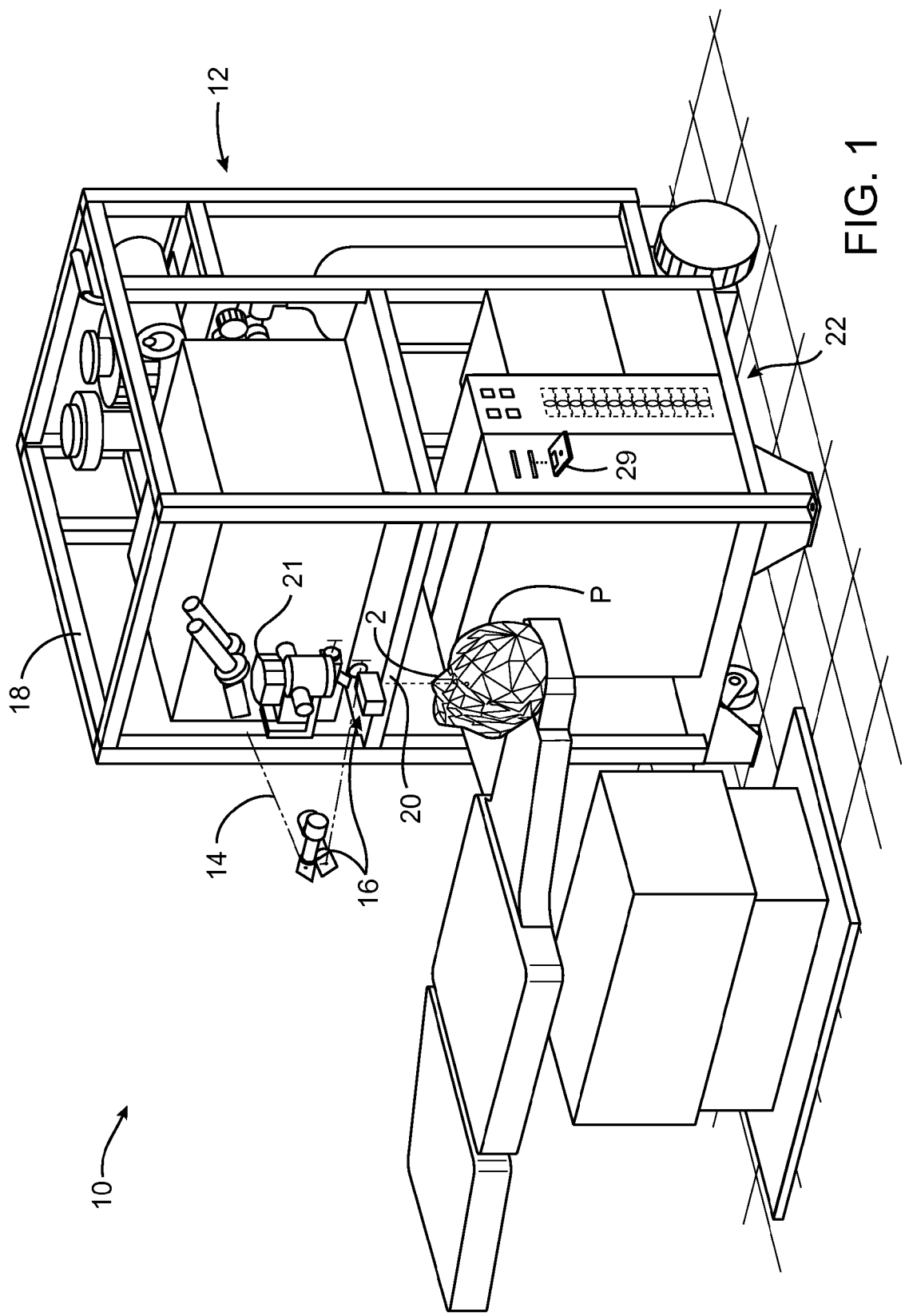
FIG. 1 is a perspective view of a laser ablation system for incorporating the present invention.

Referring now to FIG. 1, a laser eye surgery system 10 for incorporating the present invention includes a laser 12 that produces a laser beam 14. Laser delivery optics 16 are in a path of laser beam 14. Delivery optics 16 direct laser beam 14 to an eye of a patient P. A delivery optics support structure (not shown here for clarity) extends from a frame 18 supporting laser 12. An input device 20 is used to align laser system 10 in relation to an eye of a patient P. A microscope 21 is mounted on the delivery optics support structure, the microscope often being used to image a cornea of an eye. In various embodiments, a laser eye surgery system 10 includes at least some portions of a Star S4 Active Trak® Excimer Laser System available from VISX, INCORPORATED of Santa Clara, Calif.

While an input device 20 is here schematically illustrated as a joystick, a variety of input components may be used. Suitable input components may include trackballs, touch screens, or a wide variety of alternative pointing devices. Still further alternative input components include keypads, data transmission mechanisms such as an Ethernet, intranet, Internet, a modem, or the like.

A laser 12 generally comprises an excimer laser and ideally comprises an argon-fluoride laser producing pulses of laser light having a wavelength of approximately 193 nm. A pulse of laser light typically has a fixed pulse duration having a full width half maximum (FWHM) of about 15 nanoseconds during a treatment. Laser 12 is preferably designed to provide a feedback stabilized fluence at the patient's eye, delivered via delivery optics 16. The present invention may also be useful with alternative sources of electromagnetic radiation, particularly those adapted to controllably ablate a corneal tissue without causing significant damage to adjacent and/or underlying tissues of the eye. The laser system may include, but is not limited to, excimer lasers such as argon-fluoride excimer lasers (producing laser energy with a wavelength of about 193 nm), solid state lasers, including frequency multiplied solid state lasers such as flash-lamp and diode pumped solid state lasers. Exemplary solid state lasers include UV solid state lasers (approximately 193-215 nm) such as those described in U.S. Pat. Nos. 5,144,630 and 5,742,626. Laser energy may comprise a beam formed as a series of discreet laser pulses. A variety of alternative lasers might also be used. Hence, although an excimer laser is the illustrative source of an ablating beam, other lasers may be used in the present invention.

Laser 12 and delivery optics 16 will generally direct laser beam 14 to an eye of patient P under direction of a processor 22. Processor 22 will often selectively adjust laser beam 14 to expose portions of the cornea to pulses of laser energy so as to effect a predetermined sculpting of a cornea and alter refractive characteristics of an eye. In many embodiments, both laser 14 and a laser delivery optical system 16 will be under computer control of processor 22 to effect a desired laser sculpting process, with processor 22 effecting (and optionally modifying) a pattern of laser pulses. A pattern of pulses may by summarized in a treatment table listing of machine readable data of a tangible media 29. A treatment table may be adjusted according to feedback input into processor 22 from an automated image analysis system (manually input into processor 22 by a system operator) in response to feedback data provided from an ablation monitoring system feedback system. Such feedback might be provided by integrating a wavefront measurement system described below with a laser treatment system 10, and processor 22 may continue and/or terminate a sculpting treatment in response to feedback, and may optionally also modify a planned sculpting based at least in part on feedback.

Laser beam 14 may be adjusted to produce a desired sculpting using a variety of alternative mechanisms. A laser beam 14 may be selectively limited using one or more variable apertures. An exemplary variable aperture system having a variable iris and a variable width slit is described in U.S. Pat. No. 5,713,892, the full disclosure of which is incorporated herein by reference. A laser beam may also be tailored by varying a size and offset of a laser spot from an axis of an eye, as described in U.S. Pat. No. 5,683,379, and as also described in co-pending U.S. patent application Ser. No. 08/968,380, filed Nov. 12, 1997; and 09/274,999 filed Mar. 22, 1999, the full disclosures of which are incorporated herein by reference.

Still further alternatives are possible, including scanning a laser beam over a surface of an eye and controlling a number of pulses and/or dwell time at each location, as described, for example, by U.S. Pat. No. 4,665,913 (the full disclosure of which is incorporated herein by reference) and laser systems by Alcon, Bausch & Lomb, Wavelight and the like; using masks in an optical path of laser beam 14 which ablate to vary a profile of a beam incident on a cornea, as described in U.S. patent application Ser. No. 08/468,898, filed Jun. 6, 1995 (the full disclosure of which is incorporated herein by reference); hybrid profile-scanning systems in which a variable size beam (typically controlled by a variable width slit and/or variable diameter iris diaphragm) is scanned across the cornea as described in U.S. Pat. Nos. 6,319,247; 6,280,435; and 6,203,539, the full disclosures of which are incorporated herein by reference; or the like. The computer programs and control methodology for these laser pattern tailoring techniques are well described in the patent literature.

Additional components and subsystems may be included with laser system 10, as should be understood by those of skill in the art. For example, spatial and/or temporal integrators may be included to control the distribution of energy within the laser beam, as described in U.S. Pat. Nos. 5,646,791 and 5,912,779 the full disclosures of which are incorporated herein by reference. An ablation effluent evacuator/filter, and other ancillary components of the laser surgery system which are not necessary to an understanding of the invention, which may be optionally employed, need not be described in detail for an understanding of the present invention.

Processor 22 may comprise (or interface with) a conventional PC system including standard user interface devices such as a keyboard, a display monitor, and the like. Processor 22 will typically include an input device such as a magnetic or optical disk drive, an internet connection, or the like. Such input devices will often be used to download a computer executable code from a tangible storage media 29 embodying any methods of the present invention. Tangible storage media 29 may comprise a floppy disk, an optical disk, a data tape, a volatile or non-volatile memory, or the like, and a processor 22 will include memory boards and other standard components of modern computer systems for storing and executing a computer program code. Tangible storage media 29 may optionally embody wavefront sensor data, wavefront gradients, a wavefront elevation map, a treatment map, a corneal topography map, a measurement of a refraction of an eye, an ablation table, and/or instructions to adjust the amount of energy.

Figure 2:
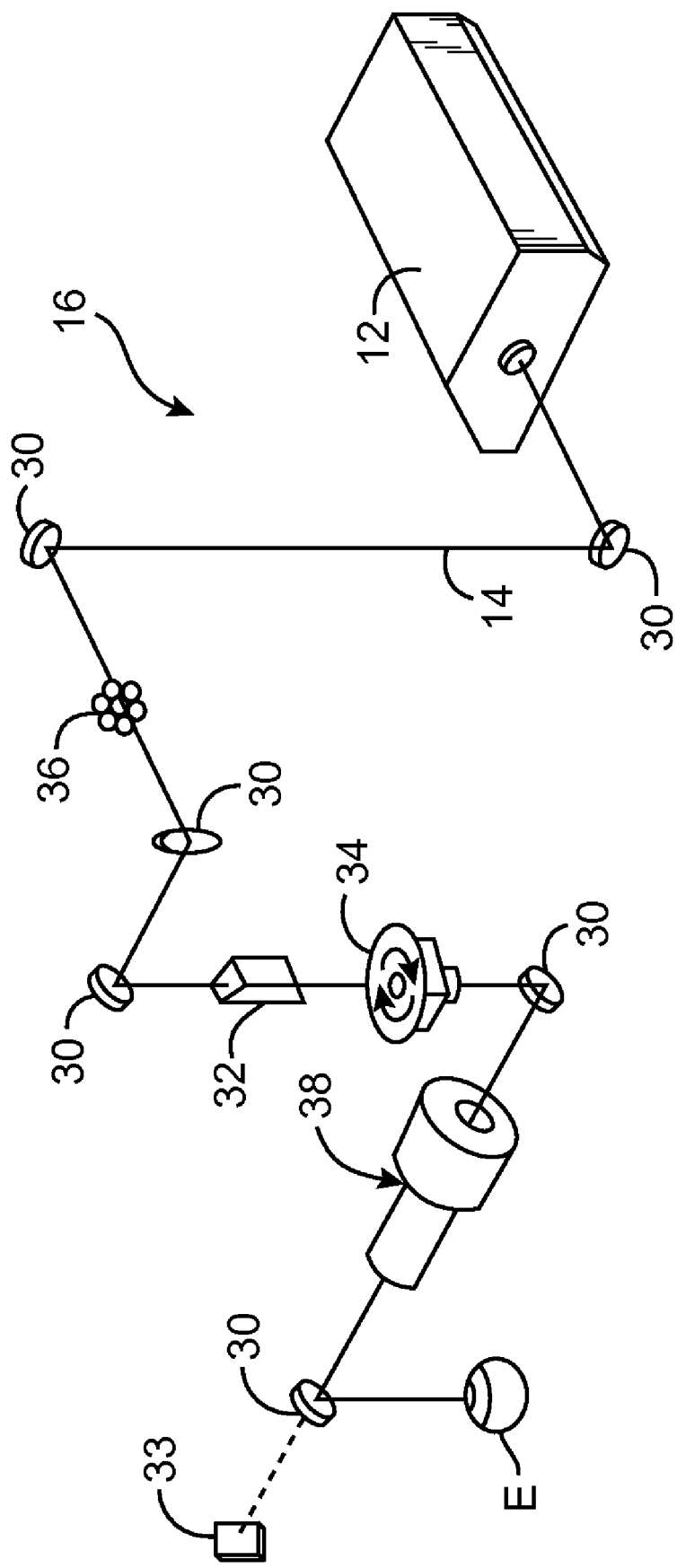
FIG. 2 schematically illustrates a laser beam delivery system for selectively directing a laser beam onto a corneal tissue according to an embodiment of the present invention.

Referring now to FIG. 2, a laser beam delivery system 16 for directing a laser beam 14 at an eye E will often include a number of mirrors 30, as well as one or more temporal integrators 32 which may adjust (or otherwise tailor) an energy distribution across a laser beam. Laser 12 will often comprise an excimer laser as described above.

In an exemplary embodiment, a variable aperture 34 changes a diameter and/or slit width to profile laser beam 14, ideally including both a variable diameter iris and a variable width slit. A prism 36 separates laser beam 14 into a plurality of beamlets, which may partially overlap on eye 2 to smooth edges of an ablation or "crater" formed from each pulse of a laser beam. An offset module 38 includes motors which vary an angular offset of an offset lens, and which also change a radial orientation of an offset. Hence, offset module 38 can selectively direct laser beam 14 at a desired lateral region of a cornea. A structure and method for using a laser beam delivery system 16 and an offset module 38 are more fully described in U.S. Pat. Nos. 6,331,177; 6,203,539; 5,912,775; and 5,646,791 the full disclosures of which are incorporated herein by reference.

In some embodiments, laser beam delivery system 16 includes a delivered energy measurement device 33 for measuring the amount of laser beam energy delivered to the eye E. For example, mirror 30 may be a semi-translucent mirror, lens or the like, to allow some amount of laser beam 14 to pass through. In many cases, measurement device 33 is used before laser beam 14 is ever applied to an eye E. For example, a sequence of test pulses of laser beam is often fired at a target positioned in the same location that the eye E will be positioned during a laser eye surgery procedure. When the sequence of test pulses is fired, measurement device 33 measures the amount of energy delivered to the patient with each pulse during the sequence. These measurements may then be used to calculate a decrease in delivered energy of laser pulses caused by accumulation of one or more substances, such as ozone, along the delivery path of laser beam 14. Measurement device 33 may also be used to measure delivered laser energy of a constant wave laser beam, which measurements may be used to calculate a decrease in energy of the beam over time. In some embodiments, measurements of delivered energy are taken, calculations are made, and laser 12 is adjusted or calibrated before a laser eye surgery is performed so as to provide stabilized delivered laser energy to eyes during laser eye surgery procedures.

The "delivery path" of laser beam 14 is depicted in FIG. 2 by the line labeled as laser beam 14. Delivery path is referred to generally in this application as any path along which a laser beam may travel from a laser beam generating device to a target. Thus, the present invention is not limited to any particular form of delivery path. Systems and methods of the invention may be used to stabilize delivered laser energy traveling along any suitable delivery path.

Figure 3:
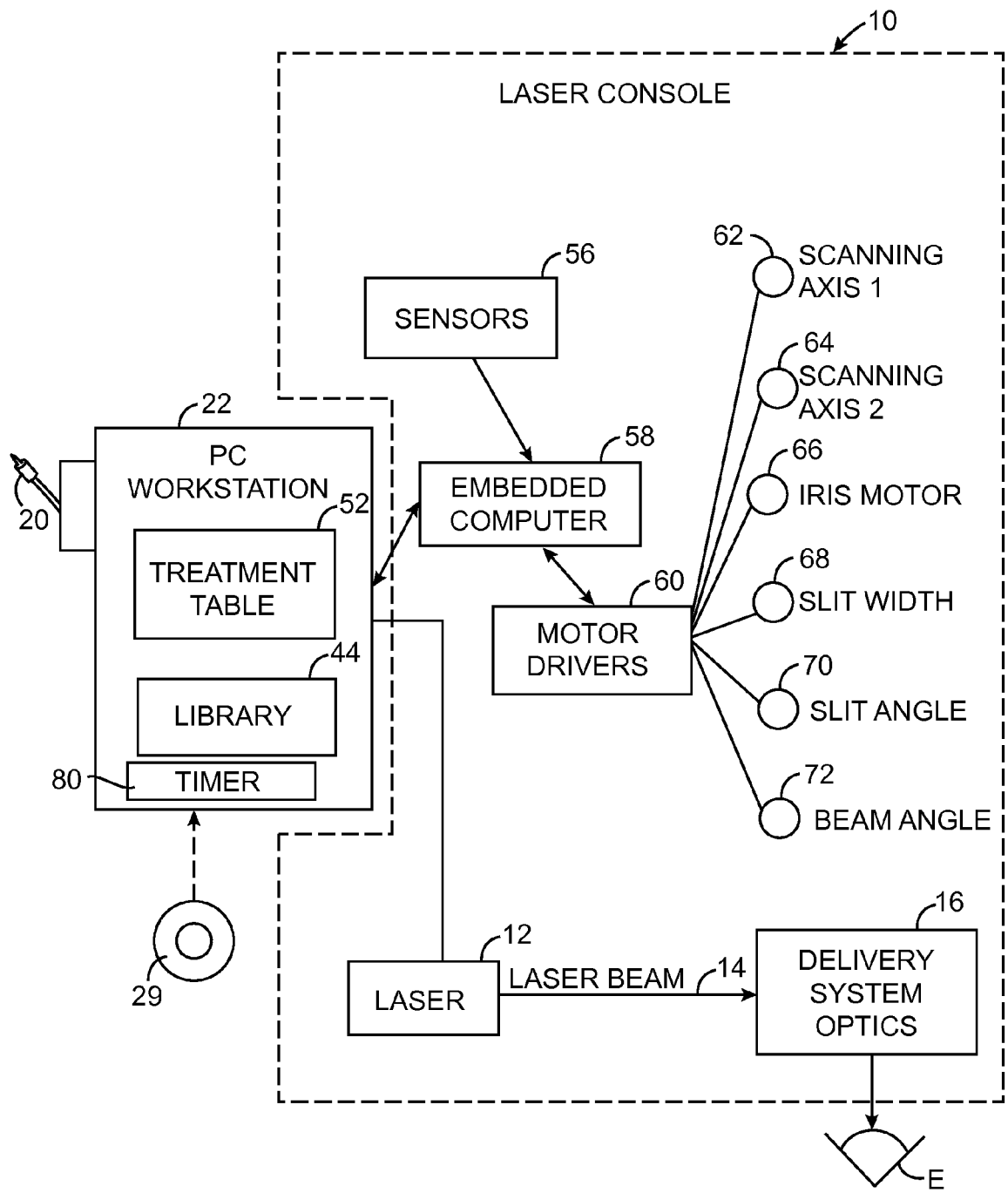
FIG. 3 is a functional block diagram illustrating a control architecture of an ablation system as in FIG. 1 according to an embodiment of the present invention.

Referring now to FIG. 3, a control system of a laser system 10 is schematically illustrated according to principles of the present invention. A processor 22 enables precise control of laser system 10 to sculpt a surface shape according to a laser treatment table 52. A processor 22, which generally comprises a PC workstation, makes use of a computer program stored on a tangible media 29 to generate treatment table 52, as described in U.S. Pat. No. 6,673,062, the full disclosure of which is incorporated herein by reference. Processor 22 includes a library 44 of treatments as described in U.S. Pat. Nos. 6,673,062 (previously incorporated by reference) and 6,245,059, the full disclosure of which is incorporated herein by reference. An embedded computer 58 within laser system 10 is in electronic communication with the PC workstation. Alternatively, a PC workstation may be embedded in laser system 10 and include an embedded processor card in communication with a PC workstation for directing an ophthalmic surgery.

Embedded computer 58 is in electronic communication with a plurality of sensors 56 and a plurality of motor drivers 60. Motor drivers 60 are coupled to an embedded computer 58 to vary a position and configuration of many of optical components of delivery optics 16 according to treatment table 52. For example, first and second scanning axes 62, 64 control a position of an offset lens to move several laser beamlets over a surface of a cornea. Iris motor 66 controls an overall diameter of a beam, and in some cases, a length of light transmitted through a variable width slit. Similarly a slit width driver 68 controls a width of a variable slit. Slit angle driver 70 controls rotation of a slit about its axis. Beam angle driver 72 controls beam rotation as effected by a temporal integrator as described above. A timer 80 controls a time interval between pulses of a laser treatment. Timer 80 measures a time interval from a previous pulse and generates an interrupt after a predetermined time interval has elapsed. Processor 22 issues a command for laser 12 to generate a pulse of laser beam 14 after various optical elements have been positioned to create a desired crater on eye E and after a measured time interval has elapsed. Treatment table 52 comprises a listing of all desired craters to be combined so as to effect a treatment therapy.

In various embodiments of the present invention, processor 22 may be used to calculate decreases in amounts of delivered laser energy to a target, to calculate adjustments in amounts of dispatched energy to compensate for the decreases in delivered energy, to provide information to laser 12 to compensate for the decreases, and/or the like. In some embodiments, a computer program stored on tangible medium 29 may be used by processor to make calculations and/or compensate for decreases in delivered energy. Methods for calculating delivered energy decreases, calculating compensatory increases, and adjusting a laser generating device are described in greater detail below.

In one aspect of the present invention, a method for stabilizing delivered laser energy involves measuring delivered laser energy over multiple laser pulses (or during a period of time, in the case of a constant wave laser), calculating a decrease in delivered energy caused by accumulation of one or more substances, such as ozone, along the laser delivery path, and adjusting a laser to compensate for the decrease. Various embodiments of such a method may include firing a number of laser pulses, measuring the pulses and using the measurements to calculate decreases in delivered energy, compensatory increases in dispatched energy and/or the like. As mentioned above, such a method may be used to calibrate a laser before performing laser eye surgery procedures. In some embodiments, one calibration of a laser generating device will be sufficient to calibrate the laser device for many laser eye surgery procedures.

Figure 4:
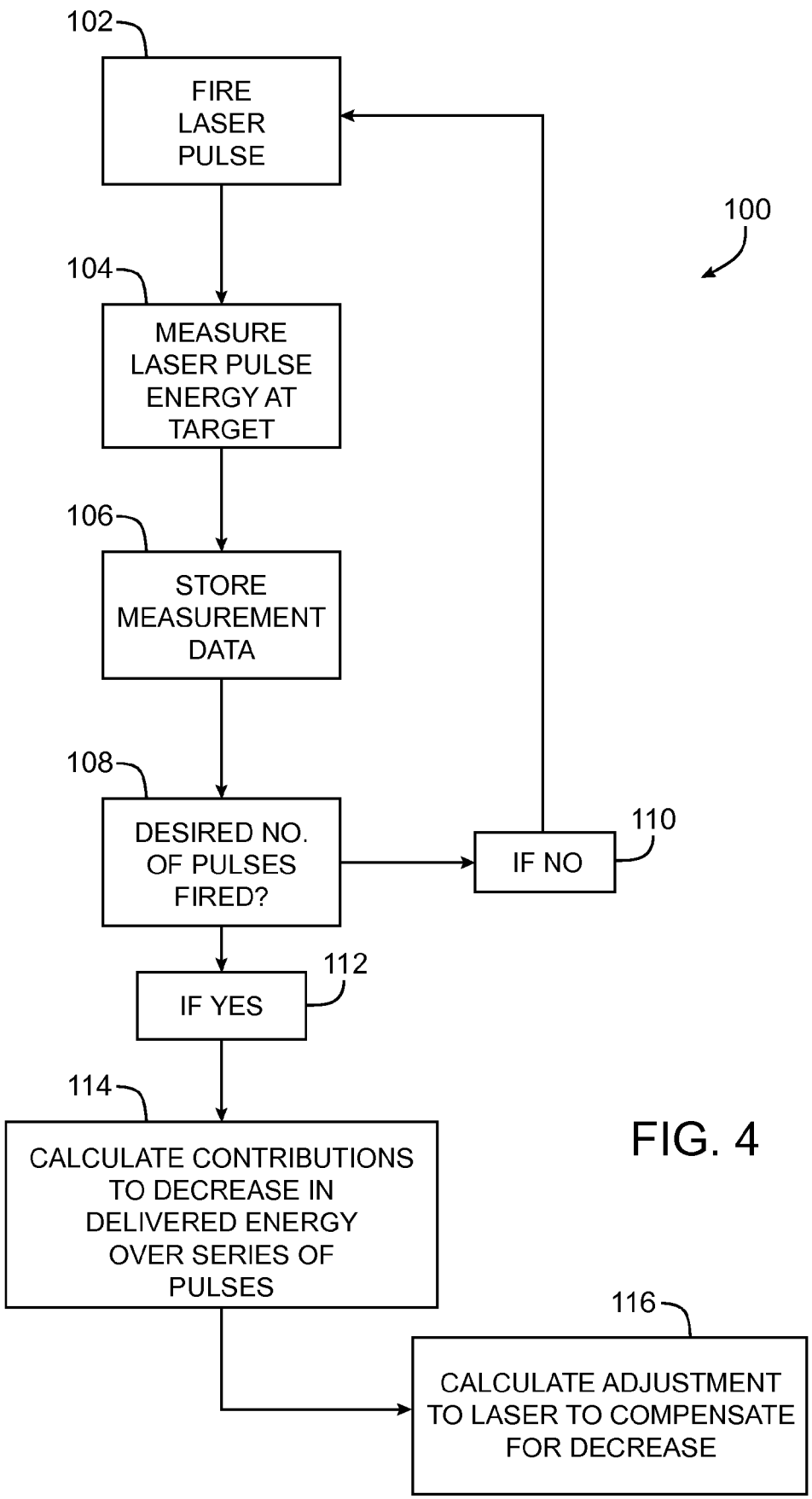
FIG. 4 is a flow chart describing a method for calibrating a laser device according to one embodiment of the present invention.

Referring now to FIG. 4, a flow diagram of one calibration method 100 for calibrating a laser device is described. The calibration method 100 generally includes firing a first laser pulse 102, measuring the energy of the laser pulse at or near a target of the laser 104, and storing the measurement data from that pulse 106. If a desired number of pulses has been fired 112, then the method proceeds to a calculating step 114. Otherwise 110, another laser pulse is fired 102, and delivered energy is measured 104 and stored 106. After a desired number of pulses has been fired 112, one or more calculations is performed 114. Such calculations include, for example, determining how much decrease in delivered energy occurs between laser pulses. In other words, one calculation may be an amount of decrease in energy that occurs in a given laser pulse as a result of accumulated substance(s), such as ozone, along the laser beam delivery path caused by the immediately preceding laser pulse. Another calculation may be an amount of dissipation of ozone (or other accumulated materials) that occurs during time delays between laser pulses. Generally, time between pulses, which allows ozone to dissipate, will decrease the effects of the accumulated ozone caused by prior laser pulses. From one or more initial calculations 114, one or more adjustments may be calculated 116 for use in programming or adjusting a laser energy generating device to compensate for the decrease in delivered laser energy at the target due to the accumulated ozone and/or other substances along the delivery path. Typically, this adjustment involves gradually increasing the energy of the laser beam provided by the laser device over time to compensate for the accumulated substances. As has been mentioned above, the method just described may be used equally well with a constant wave laser.

To compensate for the gradual build-up of ozone and/or other substances along a laser energy delivery path, the laser energy that is provided by (i.e., that leaves or is "dispatched from") the laser device is increased by a factor calculated from the predicted reduction in delivered energy. Each fired laser pulse will reduce the energy delivered by subsequent pulses by an amount, P. Counteracting this reduction in delivered energy is an increase in delivered energy caused by dissipation of ozone that occurs between laser pulses. This counteracting increase is described by the equation $C \times (E_0 - E) \times \Delta t$, where C is a diffusion constant, $E_0$ is the amount of energy delivered in the absence of ozone, E is the amount of delivered energy, and $\Delta t$ is the time interval between two laser pulses. Values for P and C may be calculated during a calibration procedure, as described above, and those values may then be used in one or more calculations to compensate for decreases in delivered energy of the laser device.

Figure 5:
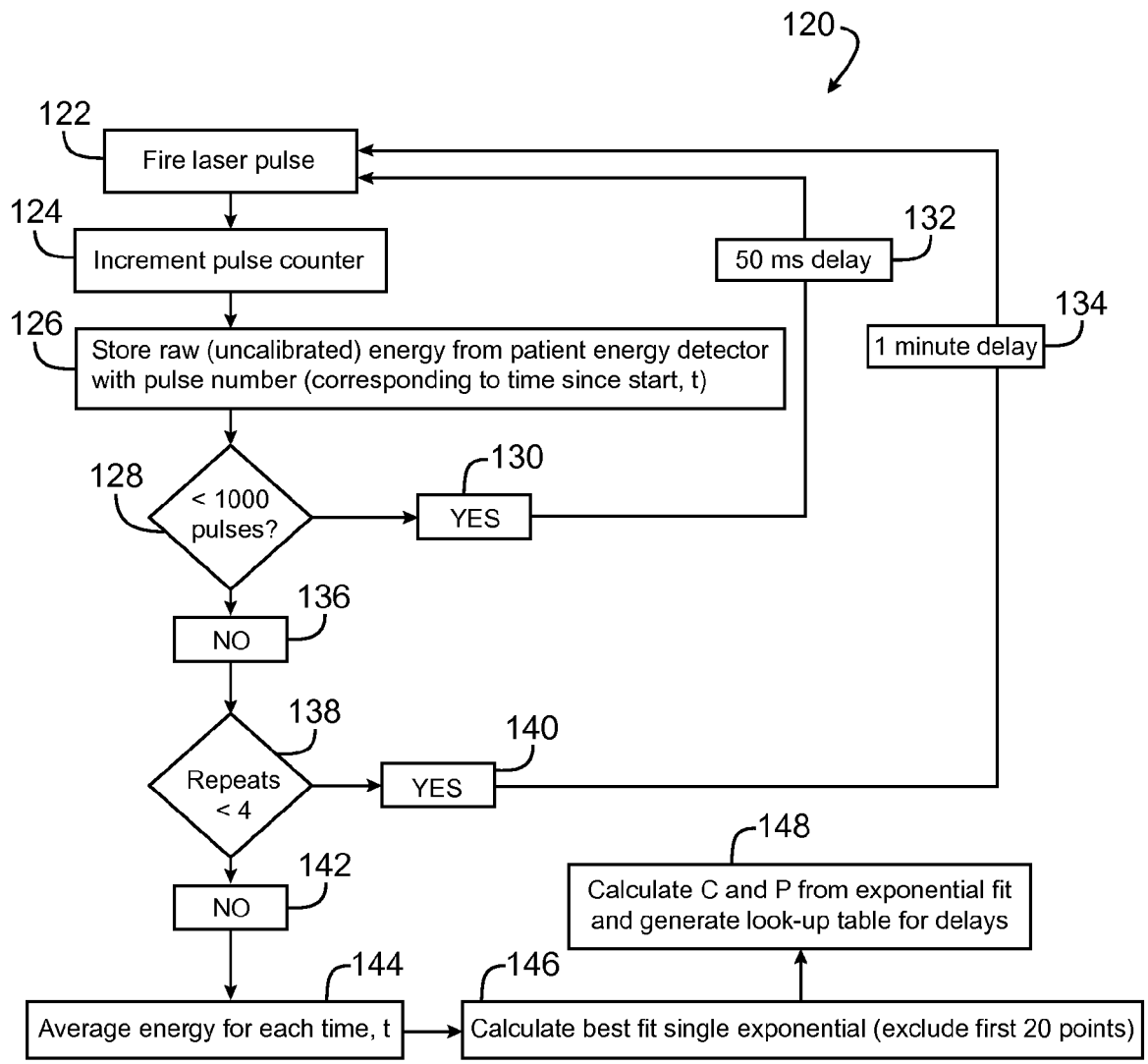
FIG. 5 is a flow chart describing another method for calibrating a laser device according to an embodiment of the present invention.

Referring now to FIG. 5, one embodiment of a calibration method 120 is described. In this embodiment, a laser pulse is fired 122, for example having an energy as close as possible to an energy that will be used for treatment of an eye. In one embodiment, this amount of energy may be determined from a most recent calibration coupled with a fluence check run shortly before the calibration. When the pulse is fired 122, a pulse counter counts the pulse 124, delivered energy data is measured and stored 126, and the system then asks if 1000 or fewer pulses have been fired 128. If yes 130, then a 50 millisecond delay occurs 132 and another laser pulse is fired 122. This process continues until 1000 pulses have been fired 136. At that point the system asks whether 4 or fewer repeats of 1000 pulses have been fired 138. If yes 140, then a one minute delay occurs 134, and another sequence of 1000 pulses is fired and measured. After 4 series of 1000 pulses are fired and measured 142, average energy for each time (t) is determined 144. The four data sets will be averaged to produce a single set of data. A single exponential will then be fit to this data 146. In one embodiment, the first 20 data points will not be used in the fit. The parameters C and P can then be easily extracted from the fit parameters 148. A look-up table may then be generated from C and P 148. This look-up table may then be used to instruct a laser device to provide a desired amount of energy in a series of laser pulses. Again, this is only one embodiment of a method for calibrating a laser device, and many variations may be made to such an embodiment without departing from the scope of the invention.

Once information is gathered during a calibration procedure, this information may be used to calibrate a laser. In other words, various methods of the invention provide for adjusting a laser device during a laser eye surgery procedure to stabilize the amount of laser energy delivered to the target—i.e., a patient's eye. Basically, the laser device is adjusted according to information gathered and calculated during the calibration procedure. In some embodiments, for example, the variables P and C are determined during calibration and these variables are then used in an equation during a laser eye surgery procedure to adjust the amount of laser energy provided by the laser device so as to stabilize delivered energy.

Figure 6:
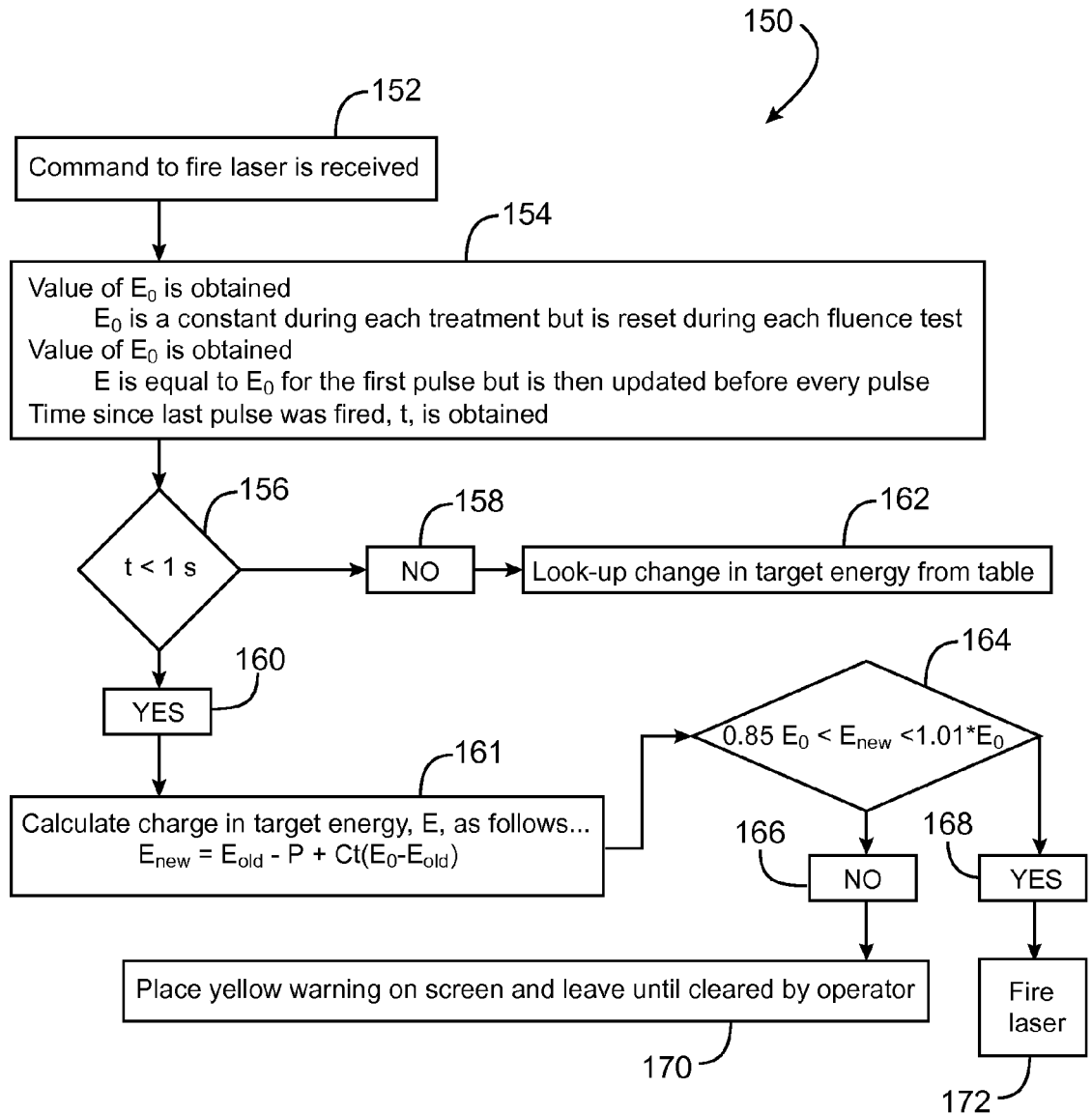
FIG. 6 is a flow chart describing a method for adjusting a laser device to stabilize delivered energy according to one embodiment of the present invention.

Referring now to FIG. 6, one exemplary method 150 for firing a laser in a laser eye surgery procedure is shown. In this embodiment, a command to fire the laser is received 152, for example by a processor couple with the laser. Next, a value of $E_0$ is obtained 154. $E_0$ is constant, and is generally the desired amount of energy fired by the laser on the first pulse. The value of E is also obtained 154. E is equal to $E_0$ for the first pulse but then changes with each subsequent pulse. E is the value of the target energy fired by the laser on each pulse, and this amount generally increases gradually during a treatment to compensate for accumulated ozone and/or other substances along the laser beam delivery path. The time since the last pulse was fired (t) is also obtained 154 at this stage. The system then asks whether t is less than approximately one second 156. If yes 160, then the system uses the equation $$E_{new}=E_{old}-P+Ct(E_0-E_{old})$$

to determine the amount of energy at which to target the next laser pulse 161. $E_{new}$ is the amount of energy at which the next laser pulse will be targeted. $E_{old}$ is the amount of energy at which the last laser pulse was targeted. P is the amount of energy by which one laser pulse decreases the delivered energy of the next subsequent laser pulse. C is a diffusion constant, and t is the time delay between two laser pulses.

In some embodiments, once $E_{new}$ is determined, it may be checked against specified limits 164, such as a minimum and maximum value related to $E_0$. In one embodiment, for example, $E_{new}$ must be greater than $0.85*E_0$ and less that $1.01*E_0$ for the laser to fire 168, 172. If $E_{new}$ does not fall within this threshold 166, then the laser does not fire, and instead a warning is provided to the user 170. Of course, this threshold check is optional, and any other threshold may be used.

In some embodiments, when t is greater than or equal to one second 158, the equation immediately above is not used to calculate the energy of the next laser pulse. Treatment interruptions of 1 second or greater may require an alternative calculation to be performed, predominantly due to the fact that such interruptions allow accumulated substances along the laser beam delivery path, such as ozone, to dissipate, thus rendering the equation explained above inapplicable. For example, in one embodiment, when t is greater than or equal to 1 second 158, then the system looks up the change in the energy of the next pulse from a table. This amount of energy of the next pulse may be referred to as the "target energy," in that it is the energy that is desired to be achieved from the laser device. Target energy, therefore is synonymous with "dispatched energy" or the other similar terms explained above. In one embodiment, a look-up table used when t is greater than or equal to 1 second uses the formula $$E_{new}=E_0(1-e^{-Ct})+E_{old}e^{-Ct}$$

to calculate $E_{new}$. In one embodiment, for example, the table may consist of 59 values corresponding to delays between 1 second and 60 seconds. Each value will be calculated by putting the time plus 0.5 second into the formula above, i.e. 1.5 seconds, 2.5 seconds, 3.5 seconds and so on, so that, for instance, a pause of between 23.00 and 23.99 seconds will use the value calculated in the table for 23.5 seconds. The calculation will be made by the laser central processing unit immediately after the command is sent by the main computer to fire (i.e. immediately before charging). The time required to perform the calculation should be negligible in comparison to the 5 millisecond delay between the command being received and the laser firing.

While the above provides a complete and accurate description of specific embodiments of the invention, several changes and adaptations of the present invention may be readily made. For example, while specific reference has been made to calibration of laser devices for use in laser eye surgery, any other suitable laser device may be calibrated using methods and systems of the present invention. In fact, since many if not all laser beams will cause an accumulation of ozone along the delivery path of the beam, systems and methods of the invention may enhance the accuracy and utility of any number of different laser devices and systems. Additionally, various embodiments of the invention may alternatively be used to enhance delivery of any beam(s) of electromagnetic radiation, and are thus not limited to use with lasers. Therefore, the above description is provided for exemplary purposes only and should not be interpreted to limit the scope of the invention as it is defined in the following claims.

What is claimed is:

1. A system for performing a laser eye surgery procedure, the system comprising:
    a laser energy generating device;
    a laser energy measuring device disposed at or near a target for measuring delivered energy of the laser energy device; and
    a processor coupled with the laser energy generating device and the laser energy measuring device for calculating an adjustment to the laser energy generating device to compensate for accumulation of one or more substances along a laser energy delivery path and for adjusting the laser energy generating device to stabilize an amount of delivered laser energy that arrives at a target of the laser eye surgery procedure.

2. A system as in claim 1, wherein the laser energy generating device provides pulsed laser energy.

3. A system as in claim 1, wherein the laser energy generating device provides constant wave laser energy.

4. A system as in claim 1, wherein the processor is calibrated before performing the laser eye surgery procedure.

5. A system as in claim 1, wherein the processor increases an amount of laser energy provided by the laser energy device to compensate for the accumulation of the substance(s) and decreases the provided laser energy to compensate for time between pulses of the laser energy, which time allows for dissipation of the substance(s).

6. A system as in claim 1, wherein the processor adjusts the laser energy generating device to compensate for accumulation of ozone along the delivery path.

* * * * *